United States Patent
Scott

(10) Patent No.: US 7,247,423 B2
(45) Date of Patent: Jul. 24, 2007

(54) METHOD TO MEASURE THE EFFECT OF TOPICALLY APPLIED AGENTS USING SKIN MAINTAINED IN ORGAN CULTURE

(75) Inventor: Ian R. Scott, Stratford upon Avon (GB)

(73) Assignee: Synergy Biosystems Ltd, Stratford upon Avon (GB)

( * ) Notice: Subject to any disclaimer, the term of this patent is extended or adjusted under 35 U.S.C. 154(b) by 176 days.

(21) Appl. No.: 11/050,955

(22) Filed: Feb. 4, 2005

(65) Prior Publication Data

US 2006/0057558 A1 Mar. 16, 2006

Related U.S. Application Data

(60) Provisional application No. 60/609,040, filed on Sep. 10, 2004.

(51) Int. Cl.
*A01N 1/00* (2006.01)
*A01N 1/02* (2006.01)

(52) U.S. Cl. ...................................... 435/1.1
(58) Field of Classification Search ............... None
See application file for complete search history.

(56) References Cited

U.S. PATENT DOCUMENTS

2003/0157074 A1* 8/2003 Mitrani ............... 424/93.21

OTHER PUBLICATIONS

Yannas et al. Science 1982;215(4529):174-176.*
Rijinkels et al. Photochemistry and Photobiology 2001;73(5):499-504.*
Chapman, S et al, "A fully differentiating epidermal model with extended viability: development and partial characterization", J. Investigative Dermatology 93, 762-768 (1989).

Tammi et al, "Histometric analysis of human skin in organ culture". J. Investigative Dermatology 73,138-140 (1979).
Henge et al, Expression of naked DNA in Human, Pig and Mouse Skin. J. Clin. Invest. 97,2911 (1996).
Flaxman et al, "Organ culture of human skin in chemically defined medium". J. Invest. Dermatol. 64, 96 (1975).
Rijnkels et al, Photoprotection by antioxidants against UVB radiation induced damage in pig skin organ culture. Radiation Research 159, 210 (2003).
Rijnkels et al, "Time and close related ultraviolet B damage in viable pig skin explants held in a newly developed organ culture system", Photochem Photobiol 73, 499 (2001).
Levine M, "The growth of adult human skin in vitro". British Journal of Dermatology 86,481 (1972).
Yasuno et al, "Organ culture of Adult Human Skin: effect of Culture temperature". J. Dermatol (Tokyo) 8, 267 (1981).

* cited by examiner

*Primary Examiner*—Ralph Gitomer
*Assistant Examiner*—Bin Shen

(57) ABSTRACT

The method employs a piece of skin of area greater than 1 cm$^2$ cultured under conditions that maintain its viability and substantially normal structure for sufficient time for topically applied test material to potentially exert an effect. The skin includes the majority of the epidermal layer plus an appropriate amount of supporting dermis. The surface of the skin is partitioned by a surface barrier film into a pattern of isolated regions to which different test materials can be subsequently topically applied in such a way that they do not significantly migrate around the edges of the skin into the culture medium. The effect of the topically applied material on the skin is determined using an appropriate method. In a variant of the method, the temperature of the culture system is maintained at or below about 30° C. to improve the skins viability and maintain a substantially normal structure. The invention encompasses effective topically applied materials identified using the methods described herein.

24 Claims, No Drawings

METHOD TO MEASURE THE EFFECT OF TOPICALLY APPLIED AGENTS USING SKIN MAINTAINED IN ORGAN CULTURE

This application claims the benefit of U.S. Provisional Application No. 60/609,040 filed Sep. 10, 2004.

FIELD OF INVENTION

The invention relates to a method of testing the effect of active ingredients on skin using an improved method of organ culture.

BACKGROUND OF THE INVENTION

There have been many attempts to create in vitro models permitting the evaluation of the effect of active agents on skin in a way that is predictive of the in vivo situation. The value of such methods is many fold. They permit elimination of live animal tests, they permit cheaper evaluation of potentially effective or toxic agents and they can permit more precise control of experimental variables than is possible using living animal or human skin. Most recent efforts to develop such systems have used cultured human epidermal cells grown on one of several possible substrates designed to mimic the dermis of skin. These systems have developed a high level of sophistication and are now available commercially, but at relatively high prices that reduce their potential areas of application. Furthermore, even the best of these models fail to reproduce the key function of skin adequately—that is they fail to generate a stratum corneum of equal impermeability to real skin. This failure to produce a good barrier is a critical failure as it means that the models cannot be used well to predict the effect of topically applied materials and, more critically, are suspect when investigation of the effect of agents on the process of stratum corneum formation are required.

An alternative to cell culture methods to create useful models is to use skin taken from animals or humans and maintained in culture. Such "organ culture" systems have the great advantage that the skin is already fully formed, with a fully functional barrier and all other cells types in their normal organization. Skin organ culture was investigated extensively as a model, especially in the 1960-80 time period. While much progress was made, the utility of the models was limited by two critical problems.

First, it proved difficult to devise culture conditions that maintained the normal structure of skin. Particular problems were the loss of tissue organization, necrosis and excessive and atypical growth of the epidermis. After much effort however conditions were devised that sustained essentially normal cellular organization—the peak of this art was represented by the work of Chapman et al ((Chapman S. et al, 1989. "A fully differentiating epidermal model with extended viability: development and partial characterization". J. Investigative Dermatology 93, 762-768) who succeeded in maintaining pig skin in culture for up to 28 days with excellent maintenance of tissue structure provided the size of the skin sample was as small as 4 mm diameter.

This success however highlighted a second critical problem that had been found by many investigators. Good maintenance of tissue organization could only be achieved by reducing the size of the piece of skin being cultured to less than about 1 sq. cm.—in fact normally less than 6 mm in diameter.

For example

Tammi et al ("Histometric analysis of human skin in organ culture". J. Investigative Dermatology 73, 138-140, 1979) found that pieces of skin of 6 mm diameter suffered degeneration after 5 days in culture Henge et al (Expression of naked DNA in Human, Pig and Mouse Skin. J. Clin. Invest. 97, 2911(1996)) cultured larger pieces of skin up 10 mm by 20 mm but could only sustain them for 24 hours Flaxman et al ("Organ culture of human skin in chemically defined medium". J. Invest. Dermatol. 64, 96 (1975)) achieved maintenance of pieces of skin of 2 mm diameter for several days Rijnkels et al (Photoprotection by antioxidants against UVB radiation induced damage in pig skin organ culture. Radiation Research 159, 210 (2003) and "Time and dose related ultraviolet B damage in viable pig skin explants held in a newly developed organ culture system", Photochem Photobiol 73, 499 (2001)) succeeded in culturing large pieces of skin up to 60 mm but observed degeneration after 48 hours This limitation had two serious consequences. First, the behavior of the culture was affected significantly by the trauma experienced at the cut edges of the skin sample. Second, it was extremely difficult to apply test agents topically to such small pieces of skin without the agents leaking around the edges of the skin sample and thereby bypassing the skin barrier. Thus analysis of large numbers of agents in such systems was impractical.

The current inventive method seeks improvements of deficiencies in the known prior art. Among the one or more problems addressed include developing an organ culture that can sustain a large sheet of skin under conditions that maintain its normal tissue organization and response to stimuli and that permits topical application of multiple agents to the skin.

SUMMARY OF INVENTION

The invention provides an in-vitro method for determining the effects on the skin of topically applied materials. Specifically, the method includes the following steps:

i. Maintaining a piece of skin of area greater than 1 $cm^2$ at the air/liquid interface of a suitable culture medium under conditions that maintain the viability and substantially normal structure of the skin for sufficient time for the topically applied material to potentially exert an effect, said skin comprising the majority of the epidermal layer plus an appropriate amount of supporting dermis and wherein the surface of said skin is partitioned by the application of a surface barrier film into a pattern of isolated regions to which different test materials can be topically applied, ii. Applying test materials to the surface of the skin in such a way that they neither significantly migrate around the edges of the skin into the culture medium nor mix with each other, and iii. Measuring the effect of the topically applied material on the skin after an appropriate time using an appropriate method.

In another preferred embodiment of the method the temperature of the culture system in step i) is maintained at or below about 30° C. to improve the viability of the skin and maintain the substantially normal structure of the skin.

In still another preferred embodiment, the skin is exposed to a chemical, physical or biological insult either prior to or after the application of test materials.

The invention also encompasses the use of materials discovered through use of the assay systems described herein that have efficacy above defined levels as measured in these assays.

DETAILED DESCRIPTION OF THE INVENTION

The inventive method involves three key steps: maintaining the skin in culture, applying test materials, and measuring the effects produced by these materials. These steps as well as optional steps are outline below.

Maintaining Skin in Organ Culture

The key challenge in making skin organ culture a practical technique is, as set out above, to maintain the essentially normal organization and response of large pieces of skin over long time periods, ideally of many days. This has not been achieved in the past despite many efforts. Without wishing to be bound by theory the inventor has come to the conclusion that one of the causes of this problem is related to the balance of the metabolic needs of the skin tissue and the rate of provision of nutrients by diffusion from the culture medium. In vivo, skin is perfused by an extensive network of blood capillaries that provide ready access of nutrients to all cells in the skin. When samples of skin are cultured ex vivo (separated from the organism) this network of capillaries is no longer functional. There is thus a much reduced availability of nutrients to the skin cells than is the case in vivo and this leads to either aberrant tissue growth and organization or to frank necrosis.

This insight explains why good preservation of tissue growth and organization in organ culture has only been achieved with very small pieces of skin. The rate of diffusion of nutrients into the skin in culture is a function of the surface area of the skin available for diffusion. Since the stratum corneum surface of the skin is essentially impermeable to nutrients the available area for diffusion of nutrients (A) to a circular piece of skin of diameter D is given by the formula $$A = \pi D^2/4 + \pi D t$$

where t is the thickness of the piece of skin being cultured.

For a typical organ culture situation, where pieces of skin of thickness of 1 mm are cultured, this formula gives the following relationship (table 1) of tissue volume (and hence metabolic demand) and total surface area, A (and hence nutrient supply).

It will readily be seen that for small tissue samples, increases in skin diameter have a major effect on the ratio of tissue volume to area of diffusion. This explains why small increases in the size of skin samples in the size range 1-4 mm so seriously adversely affects the good preservation of tissue structure. There seems to be a critical ratio of about 0.4 to 0.7 above which the tissue degrades in vitro.

This intrinsic geometrical constraint appears to limit successful skin organ culture to very small pieces of skin. The critical aspect of the current invention is however to overcome this apparently immutable constraint. The constraint can be overcome in two ways, or in a combination of the two ways.

First, if the metabolic demand of the skin can be reduced then the critical ratio of tissue volume to area available for diffusion, where loss of tissue organization and response sets in, can be increased. Secondly, if either the available surface area for diffusion or the rate of nutrient diffusion from that surface to the cells of the skin can be increased then the critical ratio will be increased.

TABLE 1

Relationship of skin sample diameter to the ratio of surface area to volume of the tissue

| D (Diameter of tissue in mm) | Volume of tissue (mm3) | A (area for diffusion in mm2) | Ratio volume of tissue to area for diffusion |
| --- | --- | --- | --- |
| 1 | 0.8 | 3.9 | 0.20 |
| 2 | 3.1 | 9.4 | 0.33 |
| 3 | 7.1 | 16.5 | 0.43 |
| 4 | 12.6 | 25.1 | 0.50 |
| 5 | 19.6 | 35.3 | 0.56 |
| 6 | 28.3 | 47.1 | 0.60 |
| 7 | 38.5 | 60.4 | 0.64 |
| 8 | 50.2 | 75.4 | 0.67 |
| 9 | 63.6 | 91.8 | 0.69 |
| 10 | 78.5 | 109.9 | 0.71 |
| 11 | 95.0 | 129.5 | 0.73 |
| 12 | 113.0 | 150.7 | 0.75 |
| 13 | 132.7 | 173.5 | 0.76 |
| 14 | 153.9 | 197.8 | 0.78 |
| 15 | 176.6 | 223.7 | 0.79 |
| 16 | 201.0 | 251.2 | 0.80 |
| 17 | 226.9 | 280.2 | 0.81 |
| 18 | 254.3 | 310.9 | 0.82 |
| 19 | 283.4 | 343.0 | 0.83 |
| 20 | 314.0 | 376.8 | 0.83 |
| 21 | 346.2 | 412.1 | 0.84 |
| 22 | 379.9 | 449.0 | 0.85 |
| 23 | 415.3 | 487.5 | 0.85 |
| 24 | 452.2 | 527.5 | 0.86 |
| 25 | 490.6 | 569.1 | 0.86 |
| 26 | 530.7 | 612.3 | 0.87 |
| 27 | 572.3 | 657.0 | 0.87 |
| 28 | 615.4 | 703.4 | 0.88 |
| 29 | 660.2 | 751.2 | 0.88 |
| 30 | 706.5 | 800.7 | 0.88 |
| 31 | 754.4 | 851.7 | 0.89 |

In either case, since the ratio of surface area for diffusion to tissue volume changes relatively slowly for tissue sizes greater than 10 mm in diameter, a small effect in either case can lead to the possibility of successful culture of pieces of skin of essentially unlimited size.

There are several ways to alter the balance between metabolic demand and diffusion of nutrients by manipulating the biochemical and physical conditions of the culture. These embodiments of the method, which can be used alone or in combination include:

Reducing the temperature of the culture system below about 30° C. This substantially reduces the metabolic demand of the tissue while having only a minor impact on diffusion rates due to the very different activation energy of the two processes as demonstrated by their respective Arrhenius plots of rate vs absolute temperature. The critical temperature is usually below about 32° C., often below 30° C. and sometimes below 25° C. The optimum temperature is in fact determined by a variety of factors including the normal metabolic demand of the tissue (which is normally higher for younger tissue) and the thickness of the tissue (which is usually determined by the amount of dermal tissue required in the culture so that, for example, a culture of skin including hair follicles or sweat gland must be thicker than a culture studying only the response of the epidermis).

Reduction of temperature of the tissue culture has been attempted in the past. Levine M. ("The growth of adult human skin in vitro". British Journal of Dermatology 86, 481 (1972)) used a temperature of 32° C. and pieces of skin of 7 mm diameter but still observed degeneration after 3-5 days. Yasuno et al ("Organ culture of Adult Human Skin: effect of Culture temperature". J. Dermatol (Tokyo) 8, 267 (1981)) also used a temperature of 32° C. with pieces of skin 1.5 mm square and sustained good tissue organization for several days. Neither paper suggests however that the reduced temperature allows culture of larger pieces of skin.

Reducing the metabolic rate of the tissue by either adding a metabolic inhibitor to the culture medium or reducing the availability of a critical nutrient Improving the rate of diffusion of nutrients into the skin by, for example Treating the skin with an enzyme such as hyaluronidase which will weaken the gel structure of the dermal tissues and hence increase the rate of diffusion of nutrients through that structure Incorporating a diffusion enhancer such as dimethyl sulphoxide into the culture medium Using a physical stimulus such as sonic waves or pulsating hydrostatic pressure to increase the speed of diffusion of nutrients into the skin Ensuring efficient mixing of the layers of culture medium that are in close contact with the skin with the bulk medium through stirring, shaking or oscillation of the culture medium Creating greater areas of interface between the skin and the culture medium by, for example, cutting through the dermis in an undulating pattern or threading porous walled tubes perfused with culture medium through the dermal tissue in a manner analogous to the technique of microdialysis.

The modifications above can be applied to pieces of skin cultured under conditions well known in the art that allow successful maintenance of small pieces of skin.

In particular use of medium which is chemically defined and free of serum discourages the phenomenon of epiboly where the epidermis migrates around the cut edge of the skin to encapsulate the entire skin sample. Suitable media include Williams E, Hams F12, Dulbecco's modification of Eagles Medium or Dulbecco's minimum essential medium.

To summarize, the modifications to conventional culture system conditions described above are chosen so as to maintain the viability and substantially normal structure of the skin in culture. By the term "maintenance of viability" I mean that the cells of the basal layer of the epidermis, in the absence of any applied test material or other stimulus such as application of irritant materials or exposure to UV light, should continue to undergo mitosis at a rate at least 20%, preferably greater than 50% and ideally greater than 75% of that found in vivo and that this maintenance of viability extends across the entire area of the tissue culture with the exception of the skin within 1 mm of the cut edge of the biopsy. By the term "substantially normal structure" I mean that the epidermis maintains clearly differentiated basal, spinous and granular layers of cells not showing histological signs of necrosis, with the total thickness of the viable epidermis not falling by greater than 70%, preferably not falling by greater than 50% and ideally not falling by greater than 30% across the entire area of the skin sample except for skin within 1 mm of the cut edge.

Optimally the skin is maintained at the air liquid interface either by being supported by a physical insert in the culture vessel or by being floated. Useful ways to achieve flotation include applying a hydrophobic layer to the upper skin surface, gluing a supporting frame to the edge of the skin or applying floating beads or other structures to the dermal side of the skin.

A preferred method is to mount a piece of skin on a rectangular plastic frame that is lighter than water. The frame dimensions are approximately 12 cm by 8 cm and it is constructed of plastic strip of dimensions approximately 3 mm×1 mm. The dermal side of the skin is glued to the 3 mm wide surface of the plastic frame with cyanoacrylate adhesive. Small gaps are left in the frame to allow air bubbles to escape, the strength of the frame being maintained by bridging the gaps with small plastic strips. This arrangement allows a 96 or 384 site template to be easily applied to the stratum corneum surface of the skin and permits easy flotation of the assembled skin on tissue culture medium. The silicone or similar barrier material of the template applied to the stratum corneum surface not only prevents wetting of the surface by the tissue culture medium but also prevents migration of the multiple test agents between treatment sites.

The culture system as described above is suitable for the maintenance of a variety of skin tissues. These include human skin obtained, for example, at post mortem or from operations such as face lifts, breast or stomach reductions, male pattern baldness reduction, circumcision etc. Rodent skin can also be used from, for example, guinea pig, rats, mice or rabbits. Of these, guinea pig is a preferred source as its mosaic pattern of hair growth reduces site to site variation of the skin. Most preferred as a source of skin is pig skin which can be obtained in large amounts as a waste product from abattoirs and particularly closely resembles human skin in its response to various stimuli.

The appropriate time for culturing the skin will depend on the application. Examples are given below.

Measurement of markers of irritation: 1-2 days

Measurement of regeneration of dermal tissue: 7-14 days

Increase in epidermal thickness: 3-6 days

Restructuring of dermal tissues: 14-28 days

The surface of skin available for treatment is greater than about 1 sq cm preferably greater than about 2 sq cm, and ideally of essentially unlimited size.

A second feature of the culture system of the inventive method is a means of ensuring that multiple and different test materials applied to different areas of the skin neither diffuse into each other nor pass into the culture medium. While several methods can be envisioned to achieve this, most are slow and cumbersome in practice. A novel and powerful way to achieve this simply and quickly is to apply to the skin surface a template of a barrier material that adheres to the skin and divides the skin surface into a pattern of distinct areas. The barrier material must be essentially impermeable to the test materials being applied to the skin surface and it must itself have minimal effect on the skin biology. One preferred material is a silicone compound that can be applied as a liquid and cured in place into a rubber. One example of such a skin compatible curable material is RTV160 from Dow silicones. The material can be applied to the skin by a variety of methods but a printing process such as use of a silk screen is particularly effective and convenient. It is also possible to apply the material through a series of nozzles drawn over the skin first in one direction then at right angles to that direction so as to create a grid.

Another preferred barrier material is a sheet of silicone rubber that is adhesive on one side and can be precut into a template prior to being applied to the skin surface.

Application of Test Materials

The barrier film described above dividing the skin surface into discrete treatment sites has an array of holes arranged in a pattern or template. Preferably, this template allows use of standard multiple tip pipetting systems to facilitate rapid and convenient application of test materials to the areas of skin defined by the template. Such automated pipetting systems are well known in the art. For example, the TPS 96 system sold by Apricot Designs Inc, 825 S. Primrose Ave, Monrovia, Calif. 91016 is suitable.

A particularly convenient arrangement is to have either 96 or 384 treatment areas of skin defined by the template so as to correspond with the wells of standard 96 or 384 multiwell plates.

However, templates including smaller numbers of treatment sites, optionally having larger surface area, are also suitable.

Regardless of whether the number of treatment sites is large, e.g., 96 sites, or relatively small, e.g., 4-8 sites, the test materials are applied in such a way that they do not migrate around the edges of the skin sample and enter the culture medium. A convenient way to prevent such migration is to include in the barrier film template a wider and/or deeper layer of barrier material around the edge of the skin. This has the double benefit of preventing leakage of applied materials around the edges of the skin and also preventing wetting of the skin surface by the surrounding culture medium.

Typically, volumes of test agents applied to the skin are approximately 2-10 microliters per sq.cm. of skin. Test agents can be left on the skin throughout the culture period, reapplied periodically during the culture period or rinsed off the skin after a period of contact with the skin. The latter approach is particularly useful when it is desired that the in vitro model should be predictive of a situation such as incorporation of active agents in a shower gel or dentifrice where in real life, the time of contact of the product with the substrate is limited.

If the test agents are reapplied or left on the skin for long periods it is often desirable to change the culture medium regularly so as to prevent accumulation in the culture medium of the small amounts of test agents that penetrate through the skin.

Measurement of the Effect of Topically Applied Materials

There are many measurement systems known in the art that are useful in determining the changes in biochemical state and/or structure of the skin in response to topically applied materials by the procedures described above. The areas of treated skin can for example be cut out, homogenized and assayed with any suitable biochemical or molecular biological method. They can also be cut out and processed by standard histological methods. In some instances direct measurement of the skin properties with minimal processing of the skin is possible, for example by measuring the autofluorescence spectrum of the skin when exposed to a UV source, or measurement of skin color by reflectance spectroscopy. Although useful in some cases, most of these techniques are time and effort intensive which is a particular problem if large numbers of test samples are involved—as would be the case with the 96 or 384 site systems described above. A novel and powerful method to measure the response of the skin in the inventive method is described below.

Skin organ cultures divided into multiple treatment areas as described above are cut into multiple suitable size pieces, which are placed together into a single cassette or other appropriate apparatus so they can be processed for histology as a single large sample. This processing can include any tissue processing technique known in the art including; fixation, dehydration and paraffin embedding; cryopreservation; embedding for electron microscopy; resin embedding, etc. The processed sample is then sectioned using standard techniques (e.g. rotary or sledge microtome or cryomicrotome). The resulting section, which contains sections of multiple areas from the original organ culture, is mounted and examined using any of the wide variety of available visualization methods including histological stains, immunohistochemical methods, in situ hybridization methods, etc.

While standard sectioning methods can be used in the above sample preparation, a preferred embodiment is to use the PSA or CryoJane methods available from Instrumedics Inc, 61 South State Street, Hackensack, N.J. 07601 which allows easy preservation of the geometrical organization of the aggregate tissue block on the sections taken.

A particularly preferred embodiment of this method applies to skin organ cultures that have been divided into 96 or 384 treatment areas as described above. In this case, the skin can be cut into strips containing a line of for example, 4, 6, 8, 12 or 16 treatment sites.

These strips are then stacked one above the other to create a composite block where the large number of treatment sites are arranged in a rectangular columnar array. When processed and sectioned this arrangement or organization of skin tissue results in a mounted section containing cross sections of all the treatment sites in a well ordered rectangular array. This regular array is particularly well suited to automated image analysis For example, where a strip of 8 treatment sites from a 384 treatment area culture of 0.5 mm thickness is chosen, the strip of skin will have dimensions of approximately 36 mm×4.5 mm×0.5 mm. There will be a total of 48 strips which when stacked will form a block of dimensions 36 mm×4.5 mm×24 mm which fits conveniently into a standard histological cassette. When cut on a rotary microtome using the PSA method to support the section, this produces a section mounted on the microscope slide of dimensions 36 mm×24 mm containing a rectangular array of 384 cross sections of the treatment sites.

The combination of combining large number of skin sites into a single histological block and use of image analysis to analyse the resulting sections makes it practical to use sophisticated histological, histochemical, immunohistochemical and molecular biological methods on many thousands of treatment sites without requiring an overwhelming amount of technician effort. A particular advantage is that multiple sections can be cut from each histological block allowing multiple different measurements to be made of each treatment area.

The appropriate histological method depends on the skin response of interest. The following Table 2 gives an exemplary but non-limiting selection of suitable methods and the application where the method would be relevant.

TABLE 2

Examples of relevant measurements for specific applications of the method

| APPLICATION OF THE ORGAN CULTURE | RELEVANT MEASUREMENT |
|---|---|
| Reversal of signs of skin ageing | Immunohistochemistry using antibody to procollagen I |
| Reduction of irritation | Immunohistochemistry using antibodies to interleukins I and VI |

TABLE 2-continued

Examples of relevant measurements for specific applications of the method

| APPLICATION OF THE ORGAN CULTURE | RELEVANT MEASUREMENT |
|---|---|
| Improve epidermal differentiation | Immunohistochemistry using antibodies to transglutaminase, filaggrin or cornifin |
| Increase epidermal thickness | Histochemistry using haematoxylin and eosin |
| Prevent UV damage | Histochemistry of sunburn cells using eosin |

Optional Steps

A further useful embodiment of the inventive method includes the step of exposing substantially the entire area of the skin to a defined physical, chemical or biological insult prior to or after applying the different test agents to the isolated regions of the skin. This is particularly useful when it is desired to measure the effect of the test agent on the response of the skin to the physical, chemical or biological insult.

An example of a physical insult is the exposure of the skin to ultraviolet light such as through the use of a controllable solar simulator that provides a measured dosage of radiation. Here the system is especially useful to compare the efficacy of the different test agents in reducing the damage done to the skin, or the response of the skin to the ultraviolet light. The skin can be irradiated before or after application of the surface barrier film and the test agents applied before or after the UV irradiation.

An example of a chemical insult is the exposure of part of or the whole skin surface to an irritant material. Examples of irritant materials include solvents such as hexadecane, a surfactant such as sodium lauryl sulfate, or an acid such as glycolic acid. The system is then used to measure the effect of test agents in reducing the hyperplasia (abnormally high keratinocyte proliferation) normally induced by such irritant treatments.

An example of a biological insult is the inoculation onto the surface of the skin of microorganisms and a source of nutrient for these microorganisms. The test agents are then compared for their ability to reduce growth of the microorganisms on the skin and/or their ability to modify the response of the skin to the microorganisms. A preferred example of this method is to inoculate the skin with microorganisms associated with dandruff such as (Malassezia) species together with a mixture of oils and other substances simulating human sebum. Test agents applied to the skin surface can either inhibit the growth of the microorganisms or reduce the irritant response that the skin experiences as a result of the microorganism growth. Both effects can be measured by the high throughput histological methods described above, with microorganism growth measured using a specific stain such as Fungi Fluor (Polysciences Inc, 400 Valley Rd, Warrington Pa.) or Gram stain and skin irritation measured by increase in IL1 or IL6 by immunohistochemistry.

Another example of a biological insult is the inclusion in the culture medium maintaining the skin of a biologically active substance that induces a change in the skin. Many biologically active molecules can be used including interleukins, growth factors, tumor necrosis factors, histamine, prostaglandins, nitric oxide, insulin, insulin like growth factors etc. A particularly useful example is the inclusion of interleukin 1 alpha in the medium which induces a hyperkeratinisation response in the skin. This system can then be used to determine the ability of topically applied materials to reduce the hyperkeratinisation response of the skin. This assay is useful in the screening for materials effective in treating or preventing acne.

The methods are very well suited to the discovery of bioactive properties of materials, particularly when it is desired to screen large numbers of materials for bioactivity or to screen large numbers of combinations of materials for bioactivity.

Useful active materials discovered using the methods described herein are those which produce a significant change in a characteristic indicator of the effect being targeted by the method, i.e., rejuvenation of aged skin. By the term "characteristic indicator" is meant some biological, biochemical or physical parameter that is measured in the test and is associated with the targeted effect. By the term "significant change" is meant changes which meet the following generic criterion.

For a particular method, i.e., an assay system, let the measured property which is selected as the "characteristic indicator" of the effect being targeted by the assay system, e.g., biological activity, be designated as X. The parameter X or characteristic indicator can be, for example, the ratio of autofluorescence of the skin at two different wavelengths when illuminated with UV light the total fluorescence intensity in the dermal region of a piece of skin sectioned and stained using an indirect immunofluorescence method using an antibody to procollagen 1 the area of stratum corneum showing abnormal staining with eosin dye in a piece of skin exposed to Interleukin 1, histologically processed and stained with eosin the intensity of fluorescent staining in pieces of skin exposed to irritant material and stained using an FITC conjugated antibody to interleukin 1.

Many other possible measured properties are envisioned within the method and several more are illustrated in the examples.

In test systems where a reduction in the parameter X is indicative that the tested material has efficacy, useful materials are defined as those that induce a reduction in X of at least 5%, preferably greater than 20% and ideally greater than 50%.

In test systems where an increase in the parameter X is indicative that the tested material has efficacy, useful materials are defined as those that increase the parameter X by at least $(X^p-X^c)/20$, preferably more than $(X^p-X^c)/5$ and ideally by more than $(X^p-X^c)/2$, where $X^p$ is the value of parameter X when a material of known biological activity (positive control) is tested in the assay and $X^c$ is the value of parameter X when no test material is tested in the assay.

The table below lists several assay systems together with the relevant measure of X and, where applicable, the relevant positive control used to determine $X^p$.

TABLE 3

Characteristic Indicators (X) of biological activity in exemplary assay systems of the invention

| Biological activity sought | Assay and measurement system | Characteristic Indicator (Parameter X) | Positive control used to define $X^p$ |
|---|---|---|---|
| Aged skin rejuvenation | See Example 1. Increase in X indicates rejuvenation | Average fluorescence intensity in 0.5 mm layer of dermis immediately below epidermis | 0.025% retinoic acid |

TABLE 3-continued

Characteristic Indicators (X) of biological activity in exemplary assay systems of the invention

| Biological activity sought | Assay and measurement system | Characteristic Indicator (Parameter X) | Positive control used to define $X^P$ |
|---|---|---|---|
| Induction of skin irritation | See Example 2. Increase in X indicates irritation | Average fluorescence intensity within viable epidermal layer | Hexadecane 100% |
| Reduction of skin irritation | See Example 5. Reduction in X indicates anti-irritant effect | Average fluorescence intensity within viable epidermal layer | Not applicable |
| Antifungal efficacy of shampoo | See Example 7 (Fungi Fluor stain). Reduction in X indicates antifungal efficacy | Average fluorescence intensity in stratum corneum | Not applicable |
| Anti acne | See Example 8. Reduction in X indicates antiacne efficacy | Average thickness of differentially stained zone at base of stratum corneum | Not applicable |
| Improved epidermal differentiation | See Example 3. Increase in X indicates improved epidermal differentiation | Area of epidermis staining positive for filaggrin | 0.5% retinyl acetate |

EXAMPLES

Particularly useful embodiments of the invention are illustrated in the following examples but are in no way intended to limit the scope or utility of the invention for evaluating a wide range of potential treatments.

Examples 1-4

Determination of the Effect of Topical Ingredients on Skin Properties

Sheets of pig skin are obtained from a local abattoir within a few hours of slaughter. The skin is transported to the laboratory in a sealed plastic bag in a mixture of ice and water. The skin is trimmed to remove subcutaneous fat and washed thoroughly first in an antimicrobial wash and then with 70% ethanol. The skin is cut into sheets approximately 12 cm×8 cm in size.

1 mm thick sheets of skin containing the entire epidermis and a layer of supporting dermis are cut using a specially designed apparatus. In this apparatus the skin is placed, stratum corneum side down, on a porous metal support linked to a vacuum pump. The skin is sucked onto the porous metal support and plastic film is applied to areas of the porous metal support that are not covered by skin so that the air pressure on the vacuum side of the skin decreases to a stable minimum not less than 0.3 bar. Strips of metal, on either side of the skin, support a rigid knife blade 1 mm above the surface of the porous metal support. Suitable knife blades include large razor blades mounted in rigid holders or microtome blades. In either case the skin is cut with a sawing action of the knife through the dermal tissue while the epidermis and layer of supporting dermis is held tightly to the porous metal support by the vacuum.

A pattern of 384 treatment sites is demarcated on the skin surface by silk screen printing using Dow silicone RTV160, with a 5 mm band of silicone surrounding the pattern of treatment sites. The sheet of skin is then mounted on a rectangular acrylic plastic frame of dimensions 12 cm×8 cm using cyanoacrylate adhesive. 2 microliter samples of test agents as set out in table 3 are applied to the demarcated sites by simultaneous pipetting from master 96 well plates using an Apricot TPS 96 pipettor—4 transfers are needed to treat all the sites. When the test samples have been applied, the skin is floated on Dulbecco's minimum essential medium supplemented with penicillin, streptomycin, fungizone, glutamine and insulin as described by Chapman et al (see above), and incubated at 25° C. degrees in an incubator humidified to 60% RH. Medium is changed every 24 hours. Test samples are reapplied every 48 hours except in example 2.

TABLE 4

Treatment compositions and conditions used in Examples 1-4.

| Treatment Type | Example 1 Aged skin rejuvenation | Example 2 Induction of skin irritation | Example 3 Improved epidermal differentiation | Example 4 Epidermal thickening |
|---|---|---|---|---|
| Number of control sites | 12 | 0 | 0 | 24 |
| Number of treatment replicates | 3 | 1 | 1 | 3 |
| Number of dose levels per test agent | 2 | 1 | 1 | 4 |
| Number of test agents | 62 | 384 | 384 | 30 |
| Incubation time in days | 14 | 2 | 7 | 10 |
| Key markers used in analysis of effect | Procollagen I deposition in dermal layer | ILI level in viable epidermis | Filaggrin intensity in granular layer | Morphometric thickness of viable epidermis |

TABLE 4-continued

Treatment compositions and conditions used in Examples 1-4.

| Treatment Type | Example 1 Aged skin rejuvenation | Example 2 Induction of skin irritation | Example 3 Improved epidermal differentiation | Example 4 Epidermal thickening |
|---|---|---|---|---|
| Method for disclosing key markers | Immunohistology using antibody to procollagen and peroxidase visualisation | Immunohistology using antibody to IL1 and alkali phospatase visualisation | Immunohistology using antibody to filaggrin and FITC conjugated second antibody | Histology using haematoxylin and eosin |
| Primary antiserum | Mouse antihuman procollagen1 cat# RDI-PROCOL1 abm-10 Research Diagnostics Inc | Rabbit anti-Human IL 1a Catalog#: RDI-IL 1Aab Research Diagnostics Inc | Monoclonal anti human filaggrin. Cat # V11018 Biomeda inc. | N/A |

After incubation for the time indicated in table 3, 48 strips of 8 treatment sites having dimensions of approximately 36 mm×4.5 mm×1 mm are cut from the sheet. These are stacked to form a block of dimensions 36 mm×4.5 mm×48 mm. The stacks are placed in histological cassettes, fixed in freshly hydrolysed paraformaldehye, dehydrated through graded alcohols, cleared in xylene, and infiltrated with paraffin. Sections are cut using a rotary microtome and transferred to large microscope slides using the PSA kit. The sections are deparaffinised and stained. In the case of examples 1-3 the sections are first blocked by incubation in a 1:10 dilution in phosphate buffered saline (PBS) of mouse serum, washed in PBS three times, then incubated in a 1:100 dilution in PBS of the primary antiserum shown in the table. Second antibody staining and development are as described in the relevant commercial kits (Sigma catalogue #'s A2304, A2556 and F5262).

In Examples 1 and 2 analysis is carried out of a high magnification image of the sections taken with a 6.1 Megapixel digital Nikon D100 camera with macro lens using the Image Pro software package. For Examples 3 and 4, the stained slides are analysed using a fluorescence microscope with motorized stage controlled by the Image Pro Plus software package from Media Cybernetics.

Example 5

Determination of the Effect of Topical Ingredients on UV Induced Irritation

Skin cultures are prepared as described for example 1-4 up to and including the stage of applying the silicone template to the skin. Prior to applying the test agents to the test sites the entire skin is exposed to UV light from a solar simulator (Sol 2, Honle UV) to a dose of 100 mJ of UVB per sq.cm. Test agents are then applied and the cultures maintained for 24 hours at 30° C. The cultures are prepared for histology as described in Examples 1-4 and sections stained and analysed as for example 2. The areas of skin underneath the silicone mask (which is essentially opaque to UVB) act as control areas.

Example 6

Determination of the Effect of Topical Ingredients on Surfactant Induced Irritation Skin cultures are prepared as described for examples 1-4 up to and including the stage of applying the silicone template to the skin. The test sites are then all exposed to a 10% solution of sodium lauryl sulphate at room temperature for 5 hours and then rinsed with distilled water. Test agents are then applied to the test areas and the skin is incubated for 48 hours at 28° C. The cultures are prepared for histology and stained for markers of irritation as in example 5.

Example 7

Determination of the Effect of Shampoo Ingredients on Dandruff

Skin cultures are prepared as described for examples 1-4 up to and including the stage of applying the silicone template to the skin. A stock solution is prepared consisting of 41% triolein, 25% oleyl acetate, 17% palmitic acid, 1.5% cholesterol, 2% cholesterol oleate, 12.5% squalene dissolved in 2:1 chloroform methanol at a total concentration of 10%. Two microlitres of this stock are applied to each of the 384 sites on the skin and the solvent allowed to evaporate. A mixture of Malasezzia Furfur, M, Restricta and M, Globosa, each at $10^7$ organisms per ml in a 2% peptone broth is prepared and 2 microlitres of the stock applied to each of the 384 sites on the skin and allowed to evaporate. The skin cultures are maintained floating on Dulbecco's minimal essential medium containing penicillin, streptomycin, glutamine and insulin but no fungizone for 24 hours at 25° C.

After 24 hours of incubation, the test samples are applied to the 384 sites (2 μl each) in a formulation consisting of a standard SLES/Betaine shampoo formula diluted to 20% with water. The samples are left in contact with the skin for 30 minutes and then the entire skin sheet is thoroughly rinsed with distilled water. The skin sheet is then incubated floating on fresh culture medium for 2 days at 25° C. before being cut into strips and processed for histology as described in examples 1-4.

Three sections cut from this block are stained as follows. One section is stained immunohistochemically using an antibody to interleukin I with streptavidin alkaline phosphatase visualization. The second is stained in the same way but using an antibody to interleukin VI. The third section is stained using a Fungi Fluor kit (Polysciences Inc, 400 Valley Rd, Warrington Pa.). All sections are photographed using 6.1 Megapixel digital Nikon D100 camera with macro lens and analysed using the Image Pro software package. The first two sections give a measurement of the extent to which the test agent reduced the irritant response triggered by the growing microorgansisms. The third section gives an independent measure of the extent to which growth of the microorganisms was inhibited by the test agent.

Example 8

Determination of Effects of Materials on Acne

Skin cultures are prepared as described for examples 1-4 up to and including the stage of applying the silicone template to the skin. When the test samples have been applied, the skin is floated on Dulbecco's minimum essential medium supplemented with penicillin, streptomycin, fungizone, glutamine and insulin as described by Chapman et al, plus interleukin 1 alpha at a concentration of 1 ng/ml and incubated at 25° C. in an incubator humidified to 60% RH. Medium is changed every 24 hours. After 96 hours the skins are fixed, cut into strips, mounted in histology cassettes and sectioned as described in examples 1-4. Sections are stained using standard haematoxylin and eosin methods and the degree of hyperkeratinisation determined by image analysis of the thickness of the differentially stained region at the base of the stratum corneum using Image Pro plus image analysis software linked to a motorized microscope and stage.

While this invention has been described with respect to specific embodiments thereof, it is apparent that numerous other forms and modifications of the invention will be obvious to those skilled in the art. This invention should be construed to cover all such obvious forms and modifications which are within the true spirit and scope of the present invention.

I claim:

1. A method for determining the effect on skin of topically applied materials comprising:
   i. maintaining a piece of skin of area greater than 1 cm² at the air/liquid interface of a suitable culture medium under conditions that maintain the viability and substantially normal structure of the skin for a period of time between 2 and 28 days at a temperature at or below 30° C., said skin comprising the majority of the epidermal layer plus an appropriate amount of supporting dermis and wherein the surface of said skin is partitioned by the application of a surface barrier film into a pattern of isolated regions to which different test materials can be topically applied;
   ii. applying test materials to the surface of the skin in such a way that they do not significantly migrate around the edges of the skin into the culture medium; and
   iii. measuring the effect of the topically applied material on the skin after an appropriate time using an appropriate method.

2. The method of claim 1 wherein the effect of the topically applied material on the skin is measured by histological, histochemical or immunohistochemical methods.

3. The method of claim 1 further comprising the step of incorporating the multiple isolated regions of the skin after treatment into single histological blocks for measurement of the effect of the topically applied material by histological, histochemical or immunohistochemical methods.

4. The method of claim 1 further comprising the step of exposing substantially the entire area of the skin to a chemical, physical or biological insult prior to or after application of the test materials of a sufficient strength to produce a change on or in the skin as measured by a histological, histochemical or immunohistochemical method.

5. The method of claim 4 wherein the effect measured of the topically applied material is associated with a reduction in the severity of the change in or on the skin produced by the insult.

6. The method of claim 4 wherein the chemical insult is a chemical irritant.

7. The method of claim 4 wherein the physical insult is exposure of the skin to ultraviolet light.

8. The method of claim 4 wherein the biological insult is inoculation of a microorganism.

9. The method of claim 8 wherein the microorganism is one associated with dandruff.

10. The method of claim 9 wherein the effect of the test material on the microorganisms and/or skin is determined by histological, histochemical or immunohistochemical methods.

11. A method for determining the effect on skin of topically applied materials comprising:
   i) Maintaining a piece of skin of area greater than 1 cm² at the air/liquid interface of a suitable culture medium at a temperature at or below 30 °C. and under conditions that maintain the viability and substantially normal structure of the skin for a period of time between 2 and 28 days, said skin comprising the majority of the epidermal layer plus an appropriate amount of supporting dermis;
   ii) Applying test materials to the surface of the skin in such a way that they do not significantly migrate around the edges of the skin into the culture medium
   iii) Measuring the effect of the topically applied material on the skin after an appropriate time using an appropriate method.

12. The method of claim 11 wherein the effect of the topically applied material on the skin is measured by histological, histochemical or immunohistochemical methods.

13. The method of claim 12 further comprising the step of incorporating the multiple isolated regions of the skin after treatment into single histological blocks for measurement of the effect of the topically applied material by histological, histochemical or immunohistochemical methods.

14. The method of claim 11 further comprising the step of exposing substantially the entire area of the skin to a chemical, physical or biological insult prior to or after application of the test materials of a sufficient strength to produce a change on or in the skin as measured by a histological, histochemical or immunohistochemical method.

15. The method of claim 14 wherein the effect measured of the topically applied material is associated with a reduction in the severity of the change in or on the skin produced by the insult.

16. The method of claim 14 wherein the chemical insult is a chemical irritant.

17. The method of claim 14 wherein the physical insult is exposure of the skin to ultraviolet light.

18. The method of claim 14 wherein the biological insult is inoculation of a microorganism.

19. The method of claim 18 wherein the microorganism is one associated with dandruff.

20. The method of claim 19 wherein the effect of the test material on the microorganisms and/or skin is determined by histological, histochemical or immunohistochemical methods.

21. The method according to claim 1 wherein the piece of skin is of a size similar to a standard 128 mm by 84 mm microplate.

22. The method according to claim 21 wherein the skin is partitioned by the application of a surface barrier film into a pattern of 96 or 384 isolated regions spaced similarly to a standard microplate to which different test materials can be topically applied.

23. The method according to claim 11 wherein the piece of skin is of a size similar to a standard 128 mm by 84 mm microplate.

24. The method according to claim 23 wherein the skin is partitioned by the application of a surface barrier film into a pattern of 96 or 384 isolated regions spaced similarly to a standard 128 mm by 84 mm microplate to which different test materials can be topically applied.

* * * * *